United States Patent [19]

Lewis

[11] Patent Number: 5,042,477

[45] Date of Patent: Aug. 27, 1991

[54] MEDICAL TUBE HOLDER

[76] Inventor: Raymond Lewis, 4968 Pauline Dr., New Orleans, La. 70126

[21] Appl. No.: 502,862

[22] Filed: Apr. 2, 1990

[51] Int. Cl.⁵ .......................... A61M 16/00; A62B 9/00
[52] U.S. Cl. ............................ 128/207.17; 128/207.14
[58] Field of Search ....................... 128/200.26, 207.14, 128/207.15, 207.16, 207.17, 911, 912, DIG. 26

[56] References Cited

U.S. PATENT DOCUMENTS

| 3,648,703 | 3/1972 | Manker | 128/DIG. 26 |
| 3,713,448 | 1/1973 | Arrott | 128/DIG. 26 |
| 4,437,463 | 3/1984 | Ackerman | 128/DIG. 26 |
| 4,838,867 | 6/1989 | Kalt et al. | 128/DIG. 26 |
| 4,896,667 | 1/1990 | Magnuson et al. | 128/DIG. 26 |

Primary Examiner—Edgar S. Burr
Assistant Examiner—Lisa E. Malvaso
Attorney, Agent, or Firm—Keaty & Keaty

[57] ABSTRACT

The present invention relates to a medical tube holder for use in securing endotracheal and similar tubes inserted in a patient's body cavity. The tube holder has an elongated tube made of elastomeric flexible material with hollow interior and a slit formed transversely to a longitudinal axis of the tubing at a middle portion of the tubing. A securing strap is threaded through the tubing with middle portion of a strap extending through the slit to form a loop through which the medical tube is inserted. The parts of the flexible fabric securing strap are brought around a body of the patient and tied together, thus retaining the medical tube in relation to the patient's body.

15 Claims, 2 Drawing Sheets

MEDICAL TUBE HOLDER

BACKGROUND OF THE INVENTION

The present invention relates to an improved medical tube holder and more particularly to a device for securing endotracheal or nasotracheal tubing to facilitate the respiratory function of a patient. The present invention can also find its use as a holder for a drainage tube which is often inserted into an incision made in a patient's skin and tissue during surgeries.

It is a conventional practice to secure such medical tubes by an adhesive tape which is wrapped around the tubing and then pressed to adhere to the skin of the patient. However, such approach is not comfortable for the patient, since removal of the adhesive tape often causes irritation and even, in severe cases, infection of the area, wherein the adhesive tape was secured.

To solve this problem, a number of medical tube holders have been suggested. For example, one type of such holders is disclosed in U.S. Pat. No. 4,437,463 issued Mar. 20, 1984 to Bernard Ackerman. The device of '463 patent provides for the use of a thin-walled elastomeric tubing having a noose formed in the tubing by passing a portion of the tubing through a ring of thick-walled tubular section. The tubing is extended about the head of the patient and secured on the back of the neck by a clamp inserted into one end of the tubing. The endotracheal tube is forced through the noose and inserted into the patient's body cavity.

However, the hook and loop attachment of the opposite ends of the tubing may not feel comfortable to the patient who is resting on his back and experiencing the pressure of the bulky connection in the back of the head.

The present invention contemplates provision of an inexpensive, easy to use, comfortable medical tube holder which is easily adjusted and secured in relation to the patient's body.

SUMMARY OF THE INVENTION

The present invention achieves its objects in a simple and straight forward manner. The medical tube holder is provided to comprise an elongated tube made of flexible elastomeric material, the tubing being hollow and of sufficient length to extend at least about a part of the patient's body. The holder further comprises an elongated flexible securing strap made of such material, as fabric and the like, which has a portion thereof extending through the length of the tubing. An aperture is formed in the middle portion of the tubing through the wall of the tubing and extends to about one half of the circumference of the tubing on the exterior side thereof.

A middle part of the securing strap is passed through the aperture to the exterior of the tubing to form a loop which serves as a retaining loop for the medical tube. Opposite ends of the flexible strap extend through the open ends of the tubing and are provided of a sufficient length to encircle the portion of the patient's body, so that the most distant ends of the strap can be secured, such as by tying, on the back of the patient's body. The aperture in the tubing is formed transversely to the longitudinal axis of the tubing on the exterior side of the tubing.

It is therefore an object of the present invention to provide a medical tube holder which is inexpensive to manufacture and easy to use.

It is another object of the present invention to provide a medical tube holder which can be easily secured on the patient's body in contact with the patient's body without inducing irritation to the skin.

It is a further object of the present invention to provide a medical tube holder which can be adjusted to the size of the body portion of the patient about which it is positioned and can be easily adjusted to a distance at which the medical tube is retained.

These and other objects of the present invention will be more apparent to those skilled in the art from the following description of the invention taken in conjunction with the accompanying drawings.

DESCRIPTION OF THE PREFERRED EMBODIMENT

Figure 2:
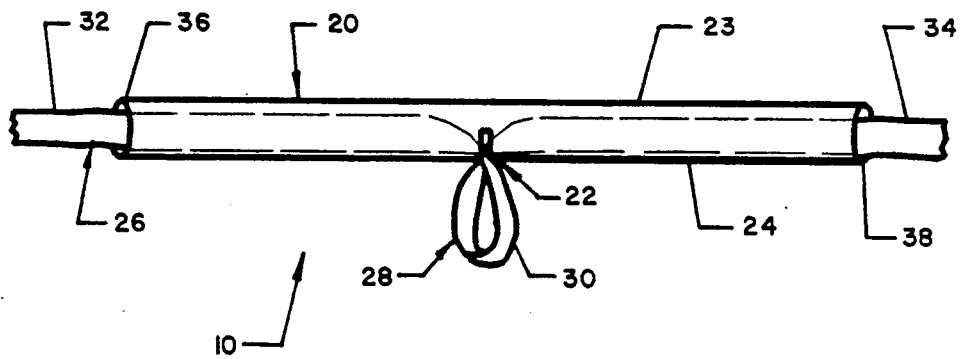
FIG. 2 is a perspective detail view of the device in accordance with the present invention.

Reference will now be made to the drawings, wherein like parts are designated by like numerals, and wherein numeral 10 designates the medical tube holder in accordance with the present invention. The holder 10 comprises an elongated hollow tubing 20 formed from a soft elastomeric plastic material which is flexible and resilient. An aperture 22 is formed in the wall of the tubing 20 transversely to its longitudinal axis, the aperture being a slit of semi-circular circumference. As can be seen in FIG. 2, the aperture 22 is formed through an exterior side 24 of the tubing 20, that is through the semicircular side which is not intended to be in close proximity to a patient's body.

A flexible elongated strip of material, such as a thin ribbon of fabric is threaded through the tubing 20 in such a manner that a mid portion 28 of the strap 26 is approximate to the slit 22 in the tubing 20. The middle portion 28 is then passed through the slit 22 into the exterior of the tubing 20 in such a manner that a loop 30 is formed from the strap 26. Opposite ends 32 and 34 of the strap 26 extend through the opposite ends 36 and 38 of the tubing 20, respectively. The length of the exposed portions of the strip 32 and 3 is made great enough so as to freely encircle the head or other body portion of the patient and be tied in a knot or bow on the back of the head, such as for example illustrated in FIG. 1.

The thickness of the strap 26 is not necessarily smaller and can be larger than the internal diameter of the tubing 20, so that the strap 26 can provide some friction but still be easily moved by ends 32 and 34, thus pulling in opposite directions the middle portion 28 of the strap 26 to make the loop 30 smaller in diameter. In a similar manner, the diameter of the loop 30 can be easily enlarged by pulling on the middle portion 28, thus pulling the strap 26 into the tubing 20 and forcing a greater portion of the strap 26 to be exposed through the slit 22.

By adjusting the length of the middle portion 28 exposed through the slit 22, the medical tube can be comfortably adjusted to the desired position when securing it on the patient's body. The fabric from which the strap 26 is made provides some friction, so as to prevent the easy slipping of the medical tube 40 into a body cavity of the patient.

The elastomeric tubing tends to close the slit 22 exerting compression force on the strap 26, thus retaining the necessary length of the exposed strap extending through the slit 22 to the exterior of the tube 20.

Figure 3:
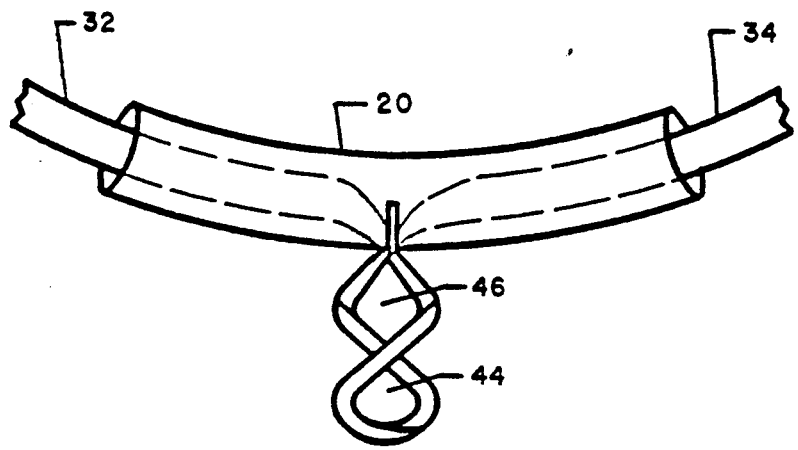
FIG. 3 is a detailed view illustrating twisting of the loop to be used for securing of a medical tube.
Figure 4:
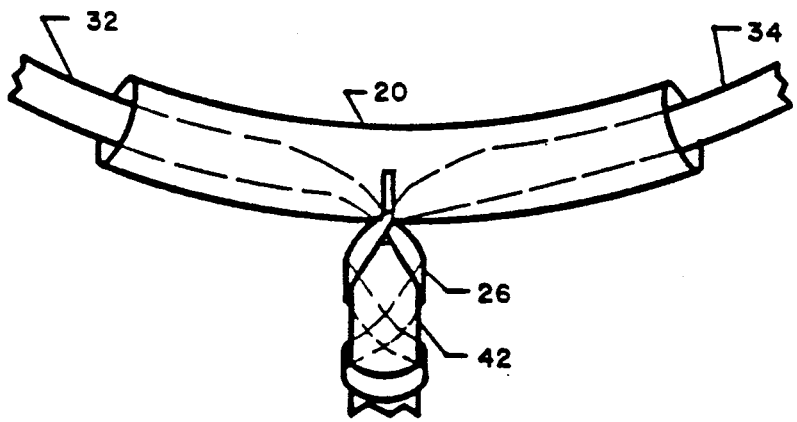
FIG. 4 is a perspective view illustrating a manner of wrapping the flexible strap about a medical tube.
Figure 5:
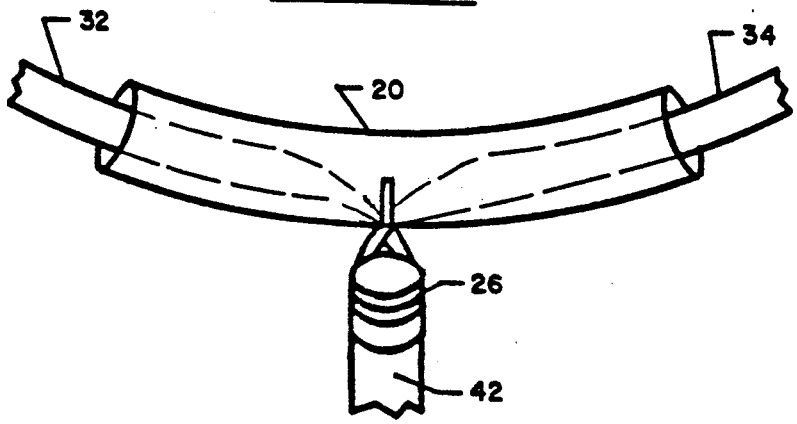
FIG. 5 illustrates tight securing of the medical tube with the strap.

In operation, a loop 30 is passed over the medical tube 42 prior to positioning of the tube in the patient's body cavity. Referring to FIG. 3 and 4, the strap middle portion 28 is seen to be twisted into two loops resembling numeral "8". The medical tube 42 is inserted through a first loop 44, which is formed by a lower circle of the numeral "8", and then is inserted through the upper circle loop 46. The strap 26, therefore has its middle portion 28 wrapped about the tube 42.

The ends 32 and 34 are pulled in opposite directions, reducing the loops 44 and 46 until they tightly encircle, while being twisted, the medical tube 42, as illustrated in FIG. 4. The tube 42 is thereby securely engaged with the device 10.

Figure 1:
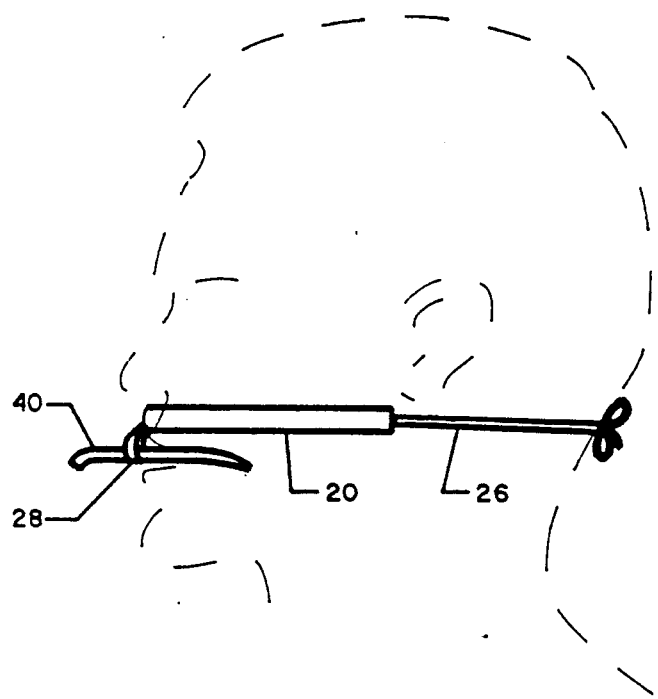
FIG. 1 is a perspective view illustrating positioning of the medical tube holder in accordance with the present invention about the head of the user, while securing an endotracheal tube.

An example of a medical tube positioning is shown in FIG. 1, wherein the medical tube is an endotracheal tube 40. The loops 44 and 46 are formed in the middle portion 28 which extends through the slit 22.

Once the tube 40 is inserted to the desired length into the mouth and throat of the patient, the tubing 20 is pressed to the face of the patient, with the inner side 23 of the tubing 20 contacting the skin of the patient. The material from which the tubing 20 is made does not induce irritation of the skin and comfortably encircles, to some degree, the head of the patient, while the strap 26 is extended around the head of the patient, bringing the ends 32 and 34 to the back of the patient's head. The ends 32 and 34 are then pulled in opposite directions to a distance ensuring comfortable positioning of the device 10 about the patient's head, while retaining the endotracheal tube 40 in a substantially stationary position in relation to the patient's mouth. The ends 32 and 34 are then secured by a knot in the back of the patient, thus allowing secure holding of the medical tube 40 about the patient's head.

Sometimes, the strap 26 becomes wet from the patient's saliva. To prevent accidental slipping of the endotracheal tube from the mouth and disengagement with the strap 26, the device 10 can be additionally secured to the tube 40 by a discreet length of an adhesive tape, such as silk tape, often used to secure needles of intravenous devices on a patient's body.

The adhesive tape is attached by one of its ends to the tubing 20 adjacent the middle part thereof on one side of the slit 22 and wrapped about the tube 40 and the strap 26 in a manner resembling cross-tying, so that the tape wraps about the tube 40 at least once. The opposite end of the tape is then secured to the tubing 20 on the opposite side of slit 22. This additional means for securing are optional, depending on the situation and on the type of the medical tube being secured.

Many changes and modifications can be made in the design of the present invention without departing from the spirit thereof. I therefore pray that my rights to the present invention be limited only by the scope of the appended claims.

I claim:

1. A medical tube holder, comprising: an elongated tubing made from elastomeric material, the tubing having a central opening extending therethrough and a longitudinal axis;
   an elongated securing strap of flexible material having a portion thereof extending inside the central opening of said tubing;
   and wherein said tubing is provided with a narrow aperture formed through a wall of the tubing facing away from the patient and transversely to the longitudinal axis approximately midway between opposite open ends of the tubing, and a part of the securing strap is passed through said aperture to form a medical tube supporting loop on exterior of the tubing, and wherein edges of the aperture exert a compression force on the securing strap, thus retaining a discreet length of the securing strap which extends through the aperture.

2. The holder of claim 1, wherein said tubing has an exterior side and an interior side, and wherein said aperture is formed on the exterior side of the tubing; so that the aperture faces away from a patient's body.

3. The holder of claim 1, wherein said aperture extends for about half of a cross circumference of the tubing.

4. The holder of claim 1, wherein said securing strap has opposite ends which extend through opposite open ends of the tubing and are adapted to extend about a patient's body and be secured together, thus securedly retaining the medical tube on the patient's body.

5. The holder of claim 1, wherein said aperture formed in the tug is a list.

6. A medical tube holder comprising:
   an elongated tubing made from an elastomeric material, the tubing having a central opening extending therethrough, an interior side and an exterior side, open opposite ends and a longitudinal axis, said elongated tubing being provided with a narrow slit formed through a wall of the tubing facing away from the patient and transversely to the longitudinal axis approximately midway between opposite ends of the tubing on the exterior side of the tubing;
   an elongated securing strap of flexible material having a portion thereof extending inside the central opening of said tubing, said strap having a middle part which is passed through said slit to form a medical tube supporting loop extending outwardly from the tubing, while edges of the slit exert a compression force on the securing strap, so as to retain a discreet length of the securing strap extending through the tubing.

7. The holder of claim 6, wherein said list extends for about a half of a cross circumference of the tubing.

8. The holder of claim 6, wherein said securing strap has opposite ends which extend through opposite open ends of the tubing and are adapted to extend about a patient's body and be secured together, thus securedly retaining the medical tube on the patient's body.

9. The apparatus of claim 6, wherein said securing strap is made of fabric.

10. A method of holding a medical tube having one end thereof inserted into a body cavity, comprising the following steps:
    providing an elongated flexible tubing having a central opening extending therethrough and a longitudinal axis; said tubing being formed with an aperture extending through a wall of the tubing transversely to the longitudinal axis;
    providing an elongated flexible securing strap extending through the central opening of the tubing with opposite ends of the strap extending exteriorly through opposite ends of the tubing, while a central part of the strap extends outwardly through said aperture forming a supporting loop;

twisting the supporting loop to resemble a numeral "8" to form supporting double loops;

extending a free end of the medical tube consecutively through each of said double loops;

positioning the tubing in contact with a patient's body;

extending the opposite ends of the strap about the patient's body while pulling the opposite ends of the strap in opposite directions until the supporting double loops tightly wrap about the medical tube;

securing the opposite ends of the strap together.

11. The method of claim 10, wherein said flexible tubing is made from elastomeric material.

12. The method of claim 10, wherein said strap is made of fabric.

13. The method of claim 10, wherein said step of positioning the flexible tubing in contact with the patient's body provides for the tubing to be positioned in such a manner than the aperture faces away from the patient's body.

14. The method of claim 10, wherein said aperture is a slit having a natural tendency to close and compress the part of the strap passing through the slits.

15. The method of claim 10, further comprising a step of additional securing of the tubing to the medical tube by wrapping a discreet length of an adhesive tape about the medical tube and attaching opposite ends of the length of the adhesive tape to the flexible tubing a distance from each other on opposite sides of the aperture.

* * * * *